(12) United States Patent
Bange et al.

(10) Patent No.: US 8,290,589 B2
(45) Date of Patent: *Oct. 16, 2012

(54) SYSTEM AND METHOD FOR RF TRANSCEIVER DUTY CYCLING IN AN IMPLANTABLE MEDICAL DEVICE

(75) Inventors: Joseph E. Bange, Eagan, MN (US);
Allan T. Koshiol, Lino Lakes, MN (US);
Karen M. Lent, Stillwater, MN (US);
Paul Holmquist, Andover, MN (US);
Thomas J. Harris, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1074 days.

This patent is subject to a terminal disclaimer.

(21) Appl. No.: 12/004,892

(22) Filed: Dec. 20, 2007

(65) Prior Publication Data

US 2008/0114412 A1 May 15, 2008

Related U.S. Application Data

(63) Continuation of application No. 11/101,196, filed on Apr. 7, 2005, now Pat. No. 7,319,903.

(60) Provisional application No. 60/560,077, filed on Apr. 7, 2004.

(51) Int. Cl.
*A61N 1/08* (2006.01)
(52) U.S. Cl. .......................................... 607/16; 607/60
(58) Field of Classification Search .................. None
See application file for complete search history.

(56) References Cited

U.S. PATENT DOCUMENTS

| 4,341,982 | A | 7/1982 | Lahti et al. |
| 4,404,972 | A | 9/1983 | Gordon et al. |
| 4,441,498 | A | 4/1984 | Nordling |
| 4,486,739 | A | 12/1984 | Franaszek et al. |
| 4,542,535 | A | 9/1985 | Bates et al. |
| 4,562,841 | A | 1/1986 | Brockway et al. |
| 4,592,360 | A | 6/1986 | Lesnick |
| 4,731,814 | A | 3/1988 | Becker et al. |
| 4,944,299 | A | 7/1990 | Silvian |
| 5,113,869 | A | 5/1992 | Nappholz et al. |
| 5,171,977 | A | 12/1992 | Morrison |
| 5,300,093 | A | 4/1994 | Koestner et al. |
| 5,314,453 | A | 5/1994 | Jeutter |
| 5,342,408 | A | 8/1994 | deCoriolis et al. |
| 5,350,411 | A | 9/1994 | Ryan et al. |
| 5,579,876 | A | 12/1996 | Adrian et al. |
| 5,766,232 | A | 6/1998 | Grevious et al. |

(Continued)

FOREIGN PATENT DOCUMENTS

JP 08-511702 A 12/1996

(Continued)

OTHER PUBLICATIONS

"U.S. Appl. No. 11/101,196 Non Final Office Action mailed Mar. 29, 2007", 8 pgs.

(Continued)

*Primary Examiner* — Kennedy Schaetzle
(74) *Attorney, Agent, or Firm* — Schwegman Lundberg & Woessner, P.A.

(57) ABSTRACT

A telemetry system is presented for enabling radio-frequency (RF) communications between an implantable medical device and an external device in a manner which reduces the power requirements of the implantable device by duty cycling its RF circuitry.

17 Claims, 4 Drawing Sheets

U.S. PATENT DOCUMENTS

| | | | |
|---|---|---|---|
| 5,807,397 A | 9/1998 | Barreras |
| 5,861,019 A | 1/1999 | Sun et al. |
| 5,881,101 A | 3/1999 | Furman et al. |
| 6,009,350 A | 12/1999 | Renken |
| 6,115,583 A | 9/2000 | Brummer et al. |
| 6,115,636 A | 9/2000 | Ryan |
| 6,155,208 A | 12/2000 | Schell et al. |
| 6,167,310 A | 12/2000 | Grevious |
| 6,169,925 B1 | 1/2001 | Villaseca et al. |
| 6,240,317 B1 | 5/2001 | Villaseca et al. |
| 6,263,246 B1 | 7/2001 | Goedeke et al. |
| 6,336,903 B1 | 1/2002 | Bardy |
| 6,388,628 B1 | 5/2002 | Dettloff et al. |
| 6,416,471 B1 | 7/2002 | Kumar et al. |
| 6,427,088 B1 | 7/2002 | Bowman, IV et al. |
| 6,456,256 B1 | 9/2002 | Amundson et al. |
| 6,472,991 B1 | 10/2002 | Schulman et al. |
| 6,482,154 B1 | 11/2002 | Haubrich et al. |
| 6,490,487 B1 | 12/2002 | Kraus et al. |
| 6,531,982 B1 | 3/2003 | White et al. |
| 6,585,644 B2 | 7/2003 | Lebel et al. |
| 6,648,821 B2 | 11/2003 | Lebel et al. |
| 6,659,948 B2 | 12/2003 | Lebel et al. |
| 6,675,045 B2 | 1/2004 | Mass et al. |
| 6,768,730 B1 | 7/2004 | Whitehill |
| 6,970,735 B2 | 11/2005 | Uber, III et al. |
| 6,993,393 B2 | 1/2006 | Von Arx et al. |
| 7,069,086 B2 | 6/2006 | Von Arx |
| 7,110,823 B2 | 9/2006 | Whitehurst et al. |
| 7,155,290 B2 | 12/2006 | Von et al. |
| 7,319,903 B2 | 1/2008 | Bange et al. |
| 7,324,012 B2 | 1/2008 | Mann et al. |
| 7,359,753 B2 | 4/2008 | Bange et al. |
| 7,519,430 B2 | 4/2009 | Arx et al. |
| 7,539,489 B1 | 5/2009 | Alexander |
| 7,573,422 B2 | 8/2009 | Harvey et al. |
| 7,664,553 B2 | 2/2010 | Earle |
| 7,738,964 B2 | 6/2010 | Von Arx et al. |
| 8,055,350 B2 | 11/2011 | Roberts |
| 2001/0047125 A1 | 11/2001 | Quy |
| 2002/0019606 A1 | 2/2002 | Lebel et al. |
| 2002/0046276 A1 | 4/2002 | Coffey et al. |
| 2002/0049480 A1 | 4/2002 | Lebel et al. |
| 2002/0065509 A1 | 5/2002 | Lebel et al. |
| 2002/0065540 A1 | 5/2002 | Lebel et al. |
| 2002/0109621 A1 | 8/2002 | Khair et al. |
| 2003/0009204 A1 | 1/2003 | Amundson et al. |
| 2003/0028902 A1 | 2/2003 | Cubley et al. |
| 2003/0050535 A1 | 3/2003 | Bowman, IV et al. |
| 2003/0107487 A1 | 6/2003 | Korman et al. |
| 2003/0114897 A1 | 6/2003 | Von Arx et al. |
| 2003/0114898 A1 | 6/2003 | Von Arx et al. |
| 2004/0047434 A1 | 3/2004 | Waltho |
| 2005/0222933 A1 | 10/2005 | Wesby |
| 2005/0240245 A1 | 10/2005 | Bange et al. |
| 2005/0283208 A1 | 12/2005 | Von Arx et al. |
| 2005/0288738 A1 | 12/2005 | Bange et al. |
| 2006/0029100 A1 | 2/2006 | Dove |
| 2006/0071756 A1 | 4/2006 | Steeves |
| 2006/0116744 A1 | 6/2006 | Von Arx et al. |
| 2006/0247736 A1 | 11/2006 | Roberts |
| 2007/0100396 A1 | 5/2007 | Freeberg |
| 2008/0215121 A1 | 9/2008 | Bange et al. |
| 2010/0121414 A1 | 5/2010 | Roberts |
| 2010/0152816 A1 | 6/2010 | Von Arx et al. |
| 2011/0313491 A1 | 12/2011 | Bange et al. |

FOREIGN PATENT DOCUMENTS

| | | |
|---|---|---|
| WO | WO-95/00202 A1 | 1/1995 |
| WO | WO-03053515 A1 | 7/2003 |
| WO | WO-03092240 A1 | 11/2003 |
| WO | WO-2005/099817 A1 | 10/2005 |
| WO | WO-2005099816 A1 | 10/2005 |
| WO | WO-2006/116004 A1 | 11/2006 |

OTHER PUBLICATIONS

"U.S. Appl. No. 11/101,196 Notice of Allowance mailed Aug. 27, 2007", 5 pgs.

"U.S. Appl. No. 11/101,196 Response filed Jun. 29, 2007 to Non Final Office Action mailed Mar. 29, 2007", 8 pgs.

"PCT Application No. PCT/US2005/011606, International Search Report and Written Opinion mailed Jul. 26, 2005", 12 pgs.

"U.S. Appl. No. 10/025,223, Communication filed Nov. 16, 2004 to Final Office Action mailed Aug. 16, 2004", 1 pg.

"U.S. Appl. No. 10/025,223, Final Office Action mailed Aug. 16, 2004", 7 pgs.

"U.S. Appl. No. 10/025,223, Final Office Action mailed Sep. 10, 2004", 7 pgs.

"U.S. Appl. No. 10/025,223, Non-Final Office Action mailed Mar. 19, 2004", 4 pgs.

"U.S. Appl. No. 10/025,223, Non-Final Office Action mailed Mar. 1, 2005", 6 pgs.

"U.S. Appl. No. 10/025,223, Notice of Allowance mailed Aug. 10, 2005", 4 pgs.

"U.S. Appl. No. 10/025,223, Response filed Jan. 10, 2005 to Final Office Action mailed Sep. 10, 2004", 10 pgs.

"U.S. Appl. No. 10/025,223, Response filed Jun. 21, 2004 to Non Final Office Action mailed Mar. 19, 2004", 9 pgs.

"U.S. Appl. No. 10/025,223, Response filed Jun. 30, 2005 to Non Final Office Action mailed Mar. 1, 2005", 10 pgs.

"U.S. Appl. No. 11/101,142, Non-Final Office Action mailed Jun. 20, 2007", 7 pgs.

"U.S. Appl. No. 11/101,142, Notice of Allowance mailed Nov. 27, 2007", 6 pgs.

"U.S. Appl. No. 11/101,142, Response filed Jun. 4, 2007 to Restriction Requirement Response mailed May 3, 2007", 7 pgs.

"U.S. Appl. No. 11/101,142, Response filed Sep. 20, 2007 to Non-Final Office Action mailed Jun. 20, 2007", 7 pgs.

"U.S. Appl. No. 11/101,142, Restriction Requirement mailed May 3, 2007", 5 pgs.

"U.S. Appl. No. 11/116,108, Advisory Action mailed Jan. 29, 2009", 3 pgs.

"U.S. Appl. No. 11/116,108, Final Office Action mailed Oct. 10, 2008", 7 pgs.

"U.S. Appl. No. 11/116,108, Non-Final Office Action mailed Mar. 20, 2008", 11 pgs.

"U.S. Appl. No. 11/116,108, Non-Final Office Action mailed Apr. 23, 2009", 7 pgs.

"U.S. Appl. No. 11/116,108, Notice of Allowance mailed Sep. 29, 2009", 8 pgs.

"U.S. Appl. No. 11/116,108, Response filed Jul. 23, 2009 to Non Final Office Action mailed Apr. 23, 2009", 7 pgs.

"U.S. Appl. No. 11/116,108, Response filed Dec. 10, 2008 to Final Office Action mailed Oct. 10, 2008", 6 pgs.

"U.S. Appl. No. 11/116,108, Response filed Jun. 20, 2008 to Non-Final Office Action mailed Mar. 20, 2008", 9 pgs.

"U.S. Appl. No. 11/325,564, Examiner Interview Summary mailed Jun. 24, 2009", 2 pgs.

"U.S. Appl. No. 11/325,584, Final Office Action mailed Oct. 24, 2008", 5 pgs.

"U.S. Appl. No. 11/325,584, Non-Final Office Action mailed Mar. 24, 2009", 5 pgs.

"U.S. Appl. No. 11/325,584, Non-Final Office Action mailed Apr. 10, 2008", 5 pgs.

"U.S. Appl. No. 11/325,584, Notice of Allowance mailed Oct. 21, 2009", 4 pgs.

"U.S. Appl. No. 11/325,584, Response filed Jan. 22, 2009 to Final Office Action mailed Oct. 24, 2008", 6 pgs.

"U.S. Appl. No. 11/325,584, Response filed Jun. 24, 2009 to Non-Final Office Action mailed Mar. 24, 2009", 9 pgs.

"U.S. Appl. No. 11/325,584, Response filed Jul. 10, 2008 to Non Final Office Action mailed Apr. 10, 2008", 9 pgs.

"European Application No. 06750873.9, Communication mailed on May 7, 2009", 2 pgs.

"European Application No. 06750873.9, Response filed Sep. 16, 2009 to Communication mailed on May 7, 2009", 7 pgs.

"European Application Serial No. 05732873.4, Communication dated Feb. 13, 2007", 3 pgs.
"European Application Serial No. 05732873.4, Communication dated Nov. 15, 2006", 2 pgs.
"European Application Serial No. 05732873.4, Response filed Aug. 18, 2007 to Communication dated Feb. 13, 2007", 13 pgs.
"European Application Serial No. 05737578.4, Communication dated Feb. 13, 2007", 3 pgs.
"European Application Serial No. 05737578.4, Response filed Aug. 10, 2007 to Communication dated Feb. 13, 2007", 15 pgs.
"International Application No. PCT/US2005/011639, International Search Report and Written Opinion mailed Aug. 26, 2005", 12 pgs.
"International Application No. PCT/US2006/014957, International Search Report and Written Opinion mailed Sep. 29, 2006", 16 pgs.
"U.S. Appl. No. 11/325,584, Notice of Allowance mailed Mar. 23, 2010", 4 pgs.
"U.S. Appl. No. 12/102,480 Non-Final Office Action mailed Aug. 18, 2010", 9 pgs.
"U.S. Appl. No. 12/691,364 Non-Final Office Action mailed Jul. 20, 2010", 7 pgs.
"European Application Serial No. 05732873.4, Office Action mailed Mar. 23, 2010", 2 Pgs.
"Japanese Application Serial No. 2007-507458, Office Action mailed Aug. 31, 2010", (w/ English Translation), 4 pgs.
"European Application Serial No. 05732873.4, Response filed Oct. 1, 2010 to Office Action mailed Mar. 23, 2010", 11 pgs.
"European Application Serial No. 057328714, Response filed Jan. 26, 2012 to Office Action mailed Nov. 17, 2011", 11 pgs.
"U.S. Appl. No. 12/102,480, Final Office Action mailed Jan. 18, 2011", 6 pgs.
"U.S. Appl. No. 12/102,480, Notice of Allowance mailed May 19, 2011", 8 pgs.
"U.S. Appl. No. 12/102,480, Response filed Apr. 18, 2011 to Final Office Action mailed Jan. 18, 2011", 9 pgs.
"U.S. Appl. No. 12/102,480, Response filed Nov. 18, 2010 to Non-Final Office Action mailed Aug. 18, 2010", 13 pgs.
"U.S. Appl. No. 12/691,364, Advisory Action mailed Mar. 30, 2011", 3 pgs.
"U.S. Appl. No. 12/691,364, Final Office Action mailed Dec. 28, 2010", 8 pgs.
"U.S. Appl. No. 12/691,364, Notice of Allowance mailed Sep. 13, 2011", 7 pgs.
"U.S. Appl. No. 12/691,364, Response filed Feb. 17, 2011 to Final Office Action mailed Dec. 28, 2010", 9 pgs.
"U.S. Appl. No. 12/691,364, Response filed Oct. 18, 2010 to Non-Final Office Action mailed Jul. 20, 2010", 11 pgs.
"U.S. Appl. No. 12/713,669, Non-Final Office Action mailed Mar. 2, 2011", 5 pgs.
"U.S. Appl. No. 12/713,669, Notice of Allowance mailed Jun. 24, 2011", 5 pgs.
"U.S. Appl. No. 12/713,669, Response filed May 16, 2011 to Non-Final Office Action mailed Mar. 2, 2011", 8 pgs.
"European Application Serial No. 05732873.4, Office Action mailed Nov. 17, 2011", 4 pgs.
US 7,680,541, 03/2010, Von et al. (withdrawn)

SYSTEM AND METHOD FOR RF TRANSCEIVER DUTY CYCLING IN AN IMPLANTABLE MEDICAL DEVICE

CROSS-REFERENCE TO RELATED APPLICATION(S)

This application is a continuation of U.S. application Ser. No. 11/101,196, filed Apr. 7, 2005, now issued as U.S. Pat. No. 7,319,903, which claims the benefit of U.S. Provisional Application No. 60/560,077, filed on Apr. 7, 2004, under 35 U.S.C. §119(e), both of which are hereby incorporated by reference.

FIELD OF THE INVENTION

This invention pertains to implantable medical devices such as cardiac pacemakers and implantable cardioverter/defibrillators. In particular, the invention relates to a system and method for implementing telemetry in such devices.

BACKGROUND

Implantable medical devices, including cardiac rhythm management devices such as pacemakers and implantable cardioverter/defibrillators, typically have the capability to communicate data with a device called an external programmer via a radio-frequency telemetry link. One use of such an external programmer is to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

Telemetry systems for implantable medical devices utilize radio-frequency (RF) energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand that can be positioned in proximity to the implanted device. The implantable device also generates and receives radio signals by means of an antenna, typically formed by a wire coil wrapped around the periphery of the inside of the device casing. Most conventional radio-frequency telemetry systems used for implantable medical devices such as cardiac pacemakers utilize inductive coupling between the antennas of the implantable device and an external programmer in order to transmit and receive RF signals. Because the induction field produced by a transmitting antenna falls off rapidly with distance, such systems require close proximity between the implantable device and a wand antenna of the external programmer in order to work properly, usually on the order of a few inches. This requirement is an inconvenience for a clinician and limits the situations in which telemetry can take place.

Wireless radio-frequency communication over greater distances requires the use of far-field telemetry. Communication using far-field radiation can take place over much greater distances, which makes it more convenient to use an external programmer. Also, the increased communication range makes possible other applications of the telemetry system such as remote monitoring of patients and communication with other types of external devices such as network access points. In order for a substantial portion of the energy delivered to an antenna to be emitted as far-field radiation, the wavelength of the driving signal should not be very much larger than the length of the antenna. Far-field radio-frequency communications with an antenna of a size suitable for use in an implantable device therefore requires a carrier in the frequency range of between a few hundred MHz to a few GHz. Active transmitters and receivers for this frequency range require special RF components (typically including SiGe or GaAs semiconductor devices) that consume a significant amount of power (typically tens of milliwatts). Implantable medical devices, however, are powered by a battery contained within the housing of the device that can only supply a limited amount of continuous power before it fails. When the battery fails in an implantable device, it must be replaced which necessitates a re-implantation procedure. Power conservation is thus an important design objective in wireless telemetry systems for implantable medical devices.

SUMMARY

A system and method are presented for enabling RF transfer of real-time data collected by an implantable medical device to an external device in a manner which reduces the power requirements of the implantable device. In an exemplary embodiment, the RF transceiver of the implantable device is duty-cycled between the times the implantable device is polled by the external device for collected data. The timing of the duty-cycling may be determined by the external device and communicated to the implantable device during the polling period.

DETAILED DESCRIPTION

Figure 1:
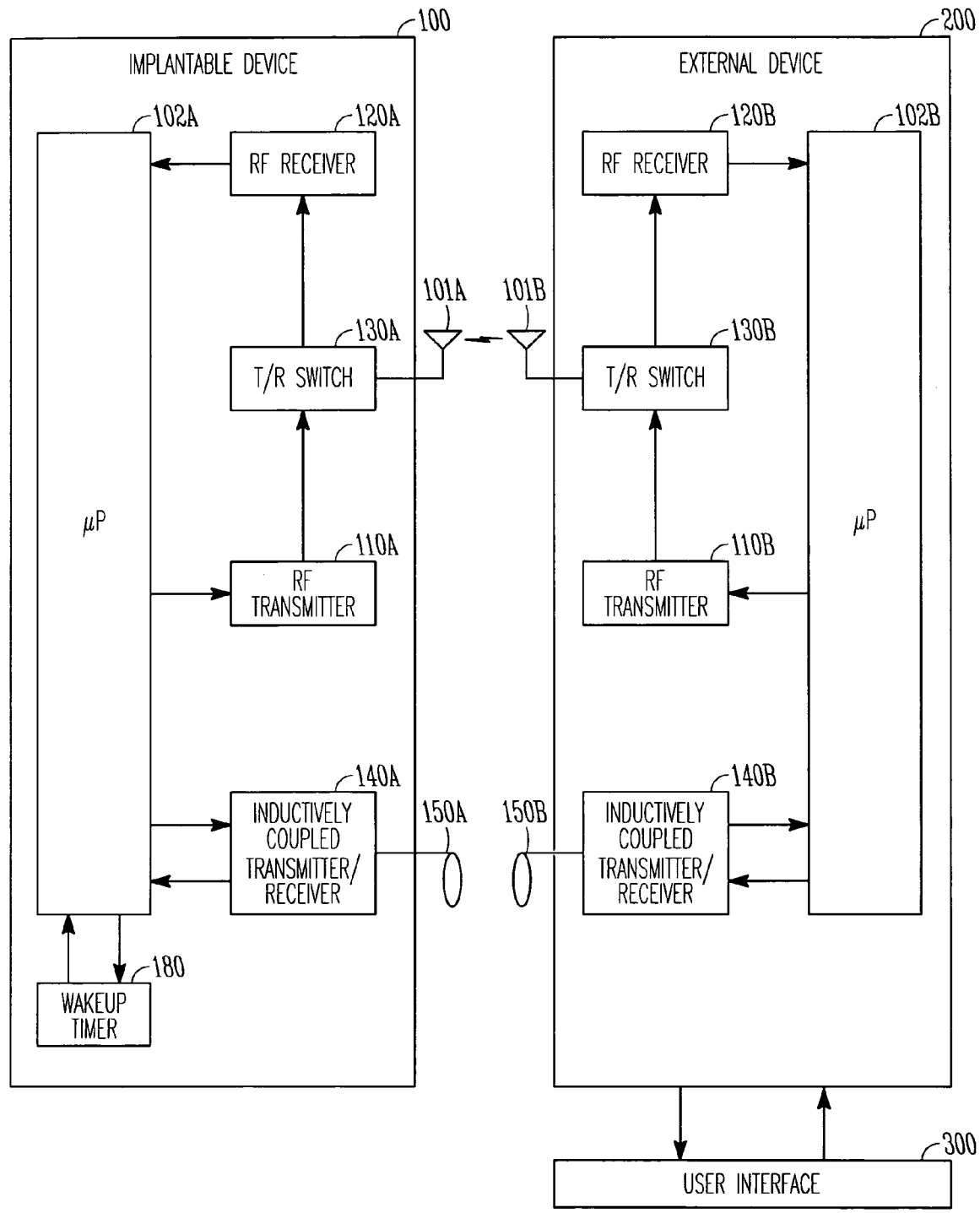
FIG. 1 is a block diagram of a telemetry system for an implantable device and an external device.

The present invention is a system and method for providing far-field RF telemetry between an implantable medical device and an external device in which power consumption by the implantable device is lessened by managing the duty cycle of the RF transmitting and receiving components. Long-range RF telemetry circuitry (i.e., the transmitter and receiver) typically requires power on the order of tens of milliwatts in order to operate. Implantable cardiac devices in use today, on the other hand, are usually designed to operate with average power in the microwatt range. This means that the RF telemetry circuitry must be duty cycled down in order to meet the power budget of such devices. Previous examples of duty cycling for implantable devices are described in U.S. Pat. Nos. 5,342,408 and 6,993,393, presently assigned to Cardiac Pacemakers, Inc., and hereby incorporated by reference.

The RF telemetry circuitry of an implantable device can either be powered up or down, referred to as awake and sleep states, respectively. One way in which duty cycling of the implantable device's RF telemetry circuitry can be implemented is a duty cycling mode where a wakeup timer is used to define periodic wakeup intervals at which the implantable device powers up its RF circuitry and listens for a transmission from an external device for a specified period of time, referred to as a wakeup window. If no transmission from the external device is received during the wakeup window while in the duty cycling mode, the implantable device returns to the sleep state until the next wakeup window. Upon receiving a transmission from the external device during the wakeup window, the implantable device enters an operational mode during which it remains in the awake state so that one or more communications sessions can be established where data is transferred between the devices. The communications sessions are established using a medium access control (MAC) protocol by which network participants contend for access to the wireless medium. After all of the communications sessions desired by either the implantable device or external device have been completed, the implantable device leaves the operational mode and goes back to the duty cycling mode.

The wakeup mechanism described above thus operates to enable the implantable device to conserve energy by remaining in an operational mode, where communications sessions can be established, only when data needs to be transferred by either the implantable device or the external device. There are certain situations, however, where although the implantable device needs to remain in the operational mode, its RF transceiver is unused for a large portion of time. One such situation is when real-time data is transferred from the implantable device to the external device. For example, the implantable device may collect physiological data such as cardiac electrograms, cardiac event markers, or various other physiological measurements and then transfer such data to the external device in real-time. ("Real-time data transfer" in this context should be taken to mean transferring the data at the same time or shortly after the data is collected.) The rate at which the data can be transferred over a telemetry channel is much greater than the rate at which the data is actually collected. One way in which data collection and data transfer can be coordinated is by having the external device periodically poll the implantable device for data while it is being collected. Each polling request from the external device initiates a communications session during which the implantable device transfers the data it has collected since the previous polling request. Between the communications sessions, the implantable device collects more data for subsequent transfer. In this scheme, however, the RF transceiver of the implantable device is only used during the communications sessions initiated by polling requests but yet must remain in an awake state between polling requests in order to receive a polling request when it is transmitted.

Presented herein is a method and system which allows duty cycling of the implantable device's RF transceiver during situations in which real-time data is transferred to an external device. In an exemplary embodiment, a telemetry system for an implantable medical device and an external device includes an antenna, an RF transceiver, and a controller incorporated into each of the implantable and external devices. The RF transceiver is interfaced to the controller in the implantable device to enable the RF transmitter and receiver to be powered up or down, referred to as an awake and sleep state, respectively. The implantable device and external device are programmed with a real-time data transfer protocol in which real-time data collected by the implantable device is transmitted to the external device in response to periodic polling requests by the external device. The implantable device and external device are further programmed so that the external device may cause the implantable device to power down its RF transceiver between polling requests by transmitting a sleep command during a communications session initiated by a polling request. The system may further include a wakeup timer incorporated into the implantable device, where the implantable device is programmed to power down its RF transceiver for a predetermined time interval as measured by the wakeup timer upon receipt of the sleep command from the external device. The length of the predetermined time interval may be either a fixed value programmed into the implantable device or may be communicated to the implantable device by the external device. In the latter instance, the length of the predetermined interval may be determined by the external device according to the type of real-time data being collected by the implantable device and/or the data transmission rate of the implantable device.

A specific embodiment of a system which implements duty-cycling of the implantable device during real-time data transfer will now be described with reference to the figures. FIG. 1 shows the primary telemetry components of an external device 200 and an implantable medical device 100. In this functional block diagram, the components are shown as being identical in each device. In this exemplary embodiment, the external device and the implantable device are microprocessor-based devices each having a controller 102a or 102b that includes a microprocessor and memory for data and program storage that supervises overall device operation as well as telemetry. Code executed by the controller also implements the duty cycle management schemes to be described below. The implantable device 100 may be a cardiac rhythm management device such as a pacemaker or implantable cardioverter/defibrillator, while the external device 200 may be an external programmer or a data-gathering device such as remote monitor. A user interface 300 (e.g., a keyboard and monitor) enables a user such as a clinician to direct the operation of the external device.

A long-range RF receiver 120a or 120b and a long-range RF transmitter 110a or 110b are interfaced to the microprocessor 102a or 102b in the implantable device and the external device, respectively. Also in each device, the transmitter and receiver are coupled to an antenna 101a or 101b through a transmit/receive switch 130a or 130b. The transmit/receive switches 130a and 130b are controlled by the microprocessor and either passes radio-frequency signals from the transmitter to the antenna or from the antenna to the receiver. To effect communications between the devices, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The implantable device also incorporates a means by which the controller can power up or power down the RF receiver and/or transmitter in order to manage duty cycles in the manner described below. A wakeup timer 180 for defining the RF duty cycle is also shown for the implantable device, and this timer can either be implemented in code executed by the controller or can be discrete components. FIG. 1 also shows an inductively coupled transmitter/receiver 140a or 140b and antenna 150a or 150b for the implantable and external devices by which communication may take place without concern for power consumption when the two devices are in close physical proximity to one another.

Figure 2:
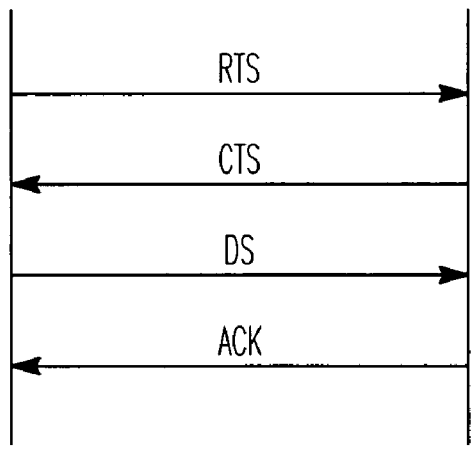
FIG. 2 illustrates a handshaking protocol for collision avoidance.

A wireless telemetry system for implantable medical devices is generally a multiple access network in which a number of network participants share the available bandwidth of the wireless medium. A medium access control (MAC) protocol may be defined which allows each network participant to acquire exclusive access to the medium before transmitting data to an intended recipient. A collision is said to occur when two or more participants attempt to transmit at the same time. In certain networks, collisions may be detected by the sender listening to the medium when a transmission is initiated to determine if other network activity is present. If a collision is detected, the sender ceases transmitting and waits for a random or defined period before trying again. Most wireless transceivers operate in a half-duplex mode, however, and cannot simultaneously transmit and listen for ongoing network activity. MAC protocols for wireless networks therefore typically use out-of-band signaling or a handshaking protocol to minimize the probability of a collision occurring. In an example of the latter type of protocol, a four-way RTS-CTS-DS-ACK exchange as illustrated by FIG. 2 is used to avoid collisions. A network participant who desires to send a message to a particular recipient first transmits a request-to-send (RTS) frame and waits a defined period of time for a clear-to-send (CTS) frame from the intended recipient. All other network participants who hear either of the RTS or CTS frames defer their transmissions. Upon receiving the CTS response, the sender can assume that the medium has been exclusively acquired and can then begin transmission of a data segment (DS) to the recipient. If the data is received without errors, the recipient responds with an acknowledge (ACK) frame which frees the medium for access by another participant.

A particular embodiment of the duty-cycling scheme for real-time data transfer will now be described for an external programmer or remote monitor (PRM/RM) and an implantable device (referred to as a pulse generator or PG) such as illustrated in FIG. 1. Real-time data is transmitted from the implantable device to the external device in response to a polling request using a handshaking protocol. The external device polls the implantable device for real-time data at specified polling intervals (e.g., 100 ms) by first transmitting an RRTS (request for RTS) frame to the implantable device. This is followed by an RTS frame from the implantable device, a CTS frame from the external device, a data segment (DS) frame from the implantable device, and an ACK frame from the external device. The sleep command, if present, is contained in the ACK frame. To support the sleep addition to the protocol the ACK message definition may be expanded to include the use of two CSB (command specific bit) codes. One code is used to indicate that the device is to remain awake (the default), the second is for the device to sleep. This is referred to below as the ACK/s or acknowledge with sleep command.

In this embodiment, the implantable device is programmed to maintain its RF transceiver in a powered up state if no sleep command is received so that the default for the PG is to stay awake unless told to go to sleep. In this way, if an ACK/s is missed by the PG, it will stay awake and the protocol will operate as designed. The penalty for this behavior is that the device may sometimes stay awake when it does not have to. If the PG were to default to going to sleep and it missed the command from the PRM to stay awake, then the protocol would make repeated attempts to communicate to a PG that is asleep and will not respond, thus wasting bandwidth that could otherwise be used by other sessions.

The external device may also be programmed to not transmit a sleep command if it has an additional command to transmit to the implantable device after receiving a response to a polling request or if the implantable device indicates it has more data to transmit when responding to a polling request. The PRM knows that it has no data to send to the device so that after a real-time data exchange, the ACK could contain the indication to go to sleep (ACK/s). When the PRM receives data to send during an interval that the PG is a sleep state, the PRM will need to wait until the next 100 ms polling period. At the 100 ms boundary the PRM would know that it has data to send and would not indicate to the PG to go to sleep during this interval. In a similar manner, if the PRM does not have data to send but receives a message that the PG has data other than real-time data (e.g., clinical history or device operations data) in response it would not indicate that the implantable device is to go to sleep for the next interval.

Figure 3A:
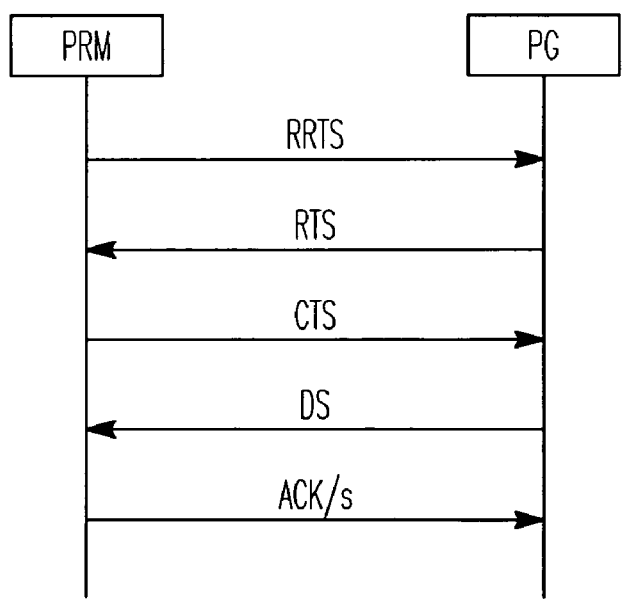
FIGS. 3A through 3D illustrate example scenarios.
Figure 3B:
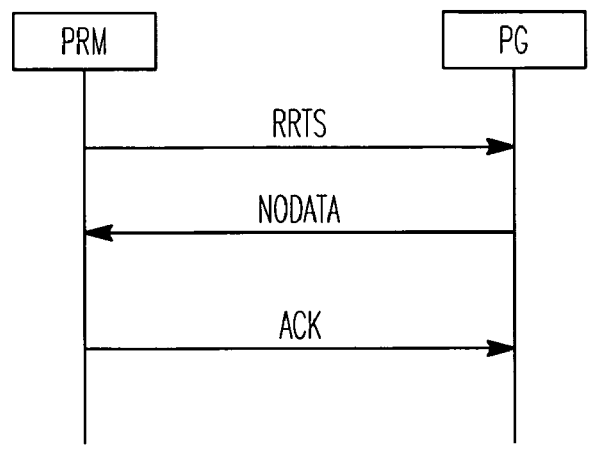
Figure 3C:
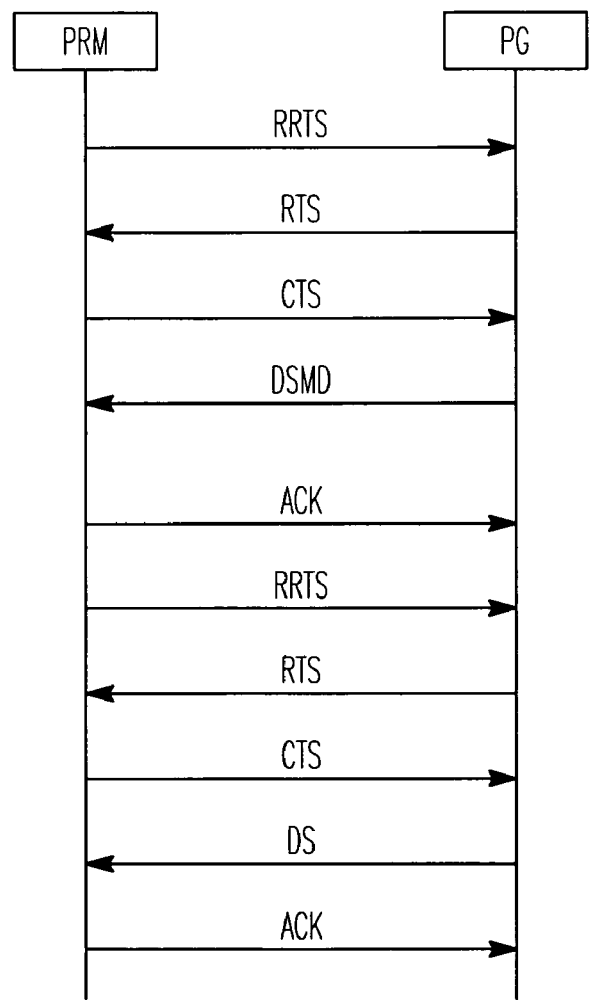
Figure 3D:
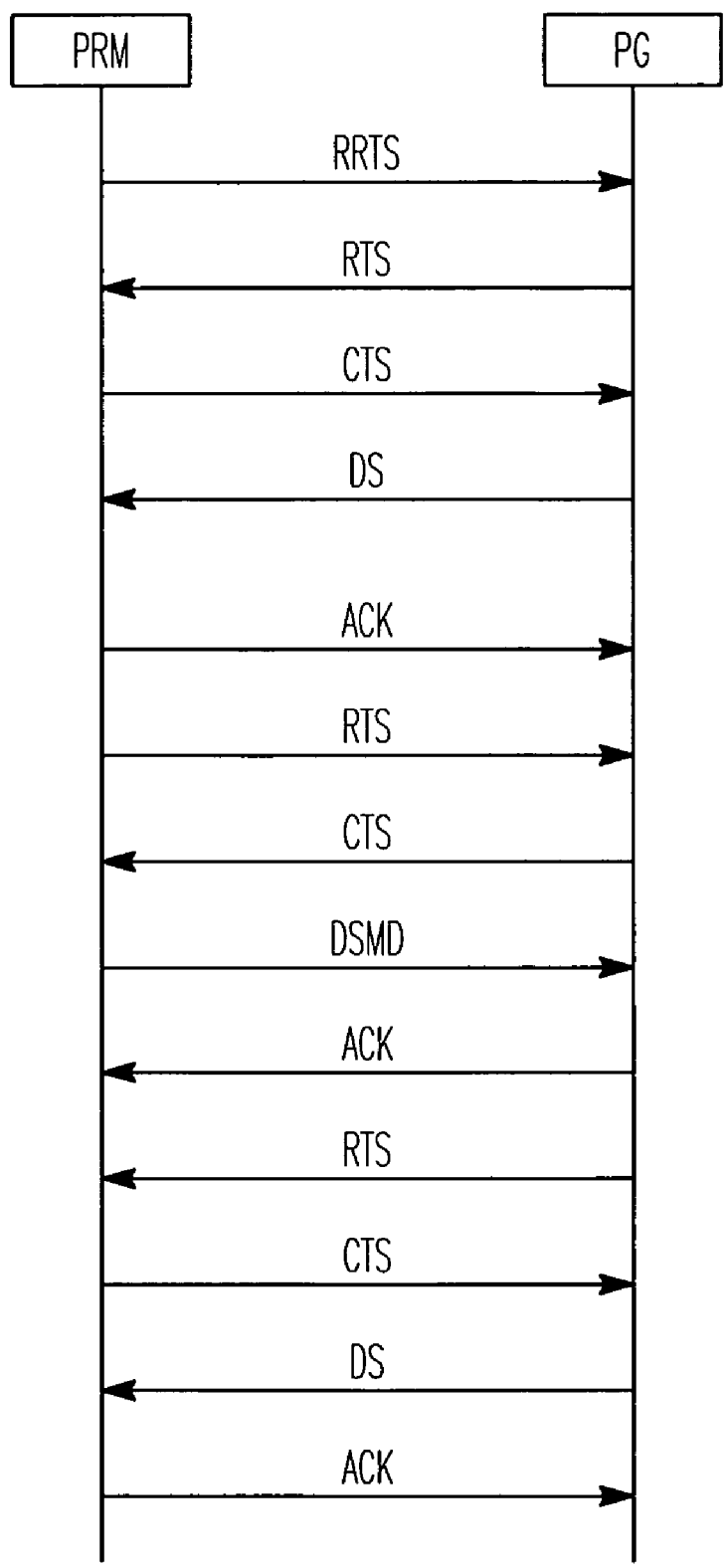

FIG. 3A illustrates the exchange between the devices when the PG has real-time data to send in response to a polling request and the PRM has no data to send. The PG is put to sleep by the ACK/s command until the next polling interval. As aforesaid, the length of the polling interval may be fixed or communicated to the PG. FIGS. 3B through 3D show examples of exchanges where the PG remains awake. In FIG. 3B, the PG responds to a polling request with a NODATA frame indicating that it has no real-time data to send. No sleep command is issued by the PRM with the acknowledgement in order to allow the PG to transmit when it does have data to send. In FIG. 3C, there is both real-time and history data in the PG. The PG indicates that it has history data to send by responding to the polling request with a DSMD frame. The subsequent ACK frame is sent by the PRM without a sleep command in order to allow both real-time data and history data to be sent without delay. In FIG. 3D, there is real-time data in the PG and the PRM has a history retrieval command to send. After receiving the real-time data in the DS frame in response to a polling request, the PRM transmits an ACK frame with no sleep command so it can transmit its history retrieval command (DSMD) which is acknowledged by the PG with an ACK frame. The PG then transmits an RTS, receives a CTS, and transmits the requested history data (DS) which is acknowledged by the PRM.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A telemetry system for an implantable medical device and an external device, comprising:

an antenna, an RF transceiver, and a controller incorporated into each of the implantable and external devices, wherein the RF transceiver is interfaced to the controller in the implantable device to enable the RF transmitter and receiver to be powered up or down;

wherein the implantable device and external device are programmed with a real-time data transfer protocol in which real-time data collected by the implantable device is transmitted to the external device in response to periodic polling requests by the external device;

a wakeup timer incorporated into the implantable device; and, wherein the implantable device is programmed to power down its RF transceiver for a predetermined time interval as measured by the wakeup timer upon receipt of a sleep command transmitted from the external device between polling requests, wherein the predetermined interval is communicated to the implantable device by the external device and is determined by the external device according to the type of real-time data being collected by the implantable device.

2. A telemetry system for an implantable medical device and an external device, comprising:
an antenna, an RF transceiver, and a controller incorporated into each of the implantable and external devices, wherein the RF transceiver is interfaced to the controller in the implantable device to enable the RF transmitter and receiver to be powered up or down;
wherein the implantable device and external device are programmed with a real-time data transfer protocol in which real-time data collected by the implantable device is transmitted to the external device in response to periodic polling requests by the external device;
a wakeup timer incorporated into the implantable device; and,
wherein the implantable device is programmed to power down its RF transceiver for a predetermined time interval as measured by the wakeup timer upon receipt of a sleep command transmitted from the external device between polling requests, wherein the predetermined interval is communicated to the implantable device by the external device and is determined by the external device according to the data transmission rate of the implantable device.

3. The system of claim 2 wherein the implantable device is programmed to maintain its RF transceiver in a powered up state if no sleep command is received.

4. The system of claim 2 wherein the external device is programmed to not transmit a sleep command if the implantable device indicates it has more data to transmit when responding to a polling request.

5. The system of claim 2 wherein the external device is programmed to not transmit a sleep command if it has an additional command to transmit to the implantable device after receiving a response to a polling request.

6. A telemetry system for an implantable medical device and an external device, comprising:
an antenna, an RF transceiver, and a controller incorporated into each of the implantable and external devices, wherein the RF transceiver is interfaced to the controller in the implantable device to enable the RF transmitter and receiver to be powered up or down;
wherein the implantable device and external device are programmed with a real-time data transfer protocol in which real-time data collected by the implantable device is transmitted to the external device in response to periodic polling requests by the external device;
wherein data is transmitted from the implantable device to the external device using a handshaking protocol which includes an RRTS frame from the external device, an RTS frame from the implantable device, a CTS frame from the external device, a data segment frame from the implantable device, and an ACK frame from the external devices;
a wakeup timer incorporated into the implantable device; and,
wherein the implantable device is programmed to power down its RF transceiver for a predetermined time interval as measured by the wakeup timer upon receipt of a sleep command transmitted from the external device between polling requests, wherein the predetermined interval is communicated to the implantable device by the external device.

7. The system of claim 6 wherein the sleep command, if present, is contained in the ACK frame.

8. A method for by which an external device may communicate with an implantable medical device comprising:
receiving real-time data collected by the implantable device in response to periodic polling requests; and
causing the implantable device to power down an RF transceiver between polling requests by transmitting a sleep command to the implantable device which causes it to power down its RF transceiver for a predetermined time interval, wherein the predetermined interval is communicated to the implantable device by the external device with the sleep command determined by the external device according to the type of real-time data being collected by the implantable device.

9. A method for by which an external device may communicate with an implantable medical device comprising:
receiving real-time data collected by the implantable device in response to periodic polling requests;
causing the implantable device to power down an RF transceiver between polling requests by transmitting a sleep command to the implantable device which causes it to power down its RF transceiver for a predetermined time interval, wherein the predetermined interval is communicated to the implantable device by the external device with the sleep command and is determined by the external device according to the data transmission rate of the implantable device.

10. The method of claim 9 wherein the implantable device is programmed to maintain its RF transceiver in a powered up state if no sleep command is received.

11. The method of claim 9 further comprising not transmitting a sleep command if the implantable device indicates it has more data to transmit when responding to a polling request.

12. The method of claim 9 further comprising not transmitting a sleep command when there is an additional command to transmit to the implantable device after receiving a response to a polling request.

13. A method for by which an external device may communicate with an implantable medical device comprising:
receiving real-time data collected by the implantable device in response to periodic polling requests, wherein data is transmitted from the implantable device to the external device using a handshaking protocol which includes an RRTS frame from the external device, an RTS frame from the implantable device, a CTS frame from the external device, a data segment frame from the implantable device, and an ACK frame from the external device, and further wherein the sleep command, if present, is contained in the ACK frame; and
causing the implantable device to power down an RF transceiver between polling requests by transmitting a sleep command to the implantable device which causes it to power down its RF transceiver for a predetermined time interval, wherein the predetermined interval is communicated to the implantable device by the external device with the sleep command.

14. An implantable medical device, comprising:
an antenna, an RF transceiver, and a controller, wherein the RF transceiver is interfaced to the controller to enable the RF transmitter and receiver to be powered up or down;
wherein the controller is programmed to communicate with an external device using a real-time data transfer protocol in which real-time data collected by the implantable device is transmitted to the external device in response to periodic polling requests by the external device;

a wakeup timer; and, wherein the controller is programmed to power down its RF transceiver for a predetermined time interval as measured by the wakeup timer upon receipt of a sleep command transmitted from the external device between polling requests, wherein the predetermined interval is communicated to the implantable device by the external device and is determined by the external device according to the type of real-time data being collected by the implantable device.

15. The device of claim 14 wherein the controller is programmed to maintain the RF transceiver in a powered up state if no sleep command is received.

16. An implantable medical device, comprising:

an antenna, an RF transceiver, and a controller, wherein the RF transceiver is interfaced to the controller to enable the RF transmitter and receiver to be powered up or down;

wherein the controller is programmed to communicate with an external device using a real-time data transfer protocol in which real-time data collected by the implantable device is transmitted to the external device in response to periodic polling requests by the external device;

a wakeup timer; and, wherein the controller is programmed to power down its RF transceiver for a predetermined time interval as measured by the wakeup timer upon receipt of a sleep command transmitted from the external device between polling requests, wherein the predetermined interval is communicated to the implantable device by the external device and is determined by the external device according to the data transmission rate of the implantable device.

17. An implantable medical device, comprising:

an antenna, an RF transceiver, and a controller, wherein the RF transceiver is interfaced to the controller to enable the RF transmitter and receiver to be powered up or down;

wherein the controller is programmed to communicate with an external device using a real-time data transfer protocol in which real-time data collected by the implantable device is transmitted to the external device in response to periodic polling requests by the external device and programmed such that data is transmitted from the implantable device to the external device using a handshaking protocol which includes an RRTS frame from the external device, an RTS frame from the implantable device, a CTS frame from the external device, a data segment frame from the implantable device, and an ACK frame from the external device, and further wherein the sleep command, if present, is contained in the ACK frame;

a wakeup timer; and, wherein the controller is programmed to power down its RF transceiver for a predetermined time interval as measured by the wakeup timer upon receipt of a sleep command transmitted from the external device between polling requests, wherein the predetermined interval is communicated to the implantable device by the external device.

* * * * *